(12) United States Patent
Bjorkesten et al.

(10) Patent No.: US 10,732,176 B2
(45) Date of Patent: Aug. 4, 2020

(54) METHOD FOR SPECIFIC IDENTIFICATION OF TARGET BIOMOLECULES

(75) Inventors: Lennart Bjorkesten, Uppsala (SE); Sofia Edlund, Uppsala (SE); Asa Hagner-McWhirter, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 630 days.

(21) Appl. No.: 14/128,379

(22) PCT Filed: Jun. 27, 2012

(86) PCT No.: PCT/SE2012/050728
§ 371 (c)(1),
(2), (4) Date: Dec. 20, 2013

(87) PCT Pub. No.: WO2013/002723
PCT Pub. Date: Jan. 3, 2013

(65) Prior Publication Data
US 2014/0134752 A1     May 15, 2014

(30) Foreign Application Priority Data
Jun. 29, 2011 (SE) ...................... 1150599

(51) Int. Cl.
*G01N 33/543* (2006.01)
*G01N 33/561* (2006.01)
*G01N 27/447* (2006.01)

(52) U.S. Cl.
CPC ..... *G01N 33/543* (2013.01); *G01N 27/44726* (2013.01); *G01N 33/561* (2013.01)

(58) Field of Classification Search
None
See application file for complete search history.

(56) References Cited

U.S. PATENT DOCUMENTS

| | | | |
|---|---|---|---|
| 7,155,050 B1 * | 12/2006 | Sloge et al. | 382/133 |
| 7,642,089 B2 * | 1/2010 | Pieper et al. | 435/288.6 |
| 7,745,640 B2 * | 6/2010 | Czerney et al. | 548/455 |
| 7,881,517 B2 * | 2/2011 | Sloge et al. | 382/133 |
| 2005/0186642 A1 * | 8/2005 | Tacha | G01N 33/57492 435/7.9 |
| 2007/0161116 A1 * | 7/2007 | Copse | 436/172 |
| 2008/0166030 A1 * | 7/2008 | Morris | G01N 27/44721 382/128 |
| 2008/0233660 A1 * | 9/2008 | Uhlen | G01N 33/533 436/518 |

FOREIGN PATENT DOCUMENTS

| | | |
|---|---|---|
| WO | 2010010158 A1 | 1/2010 |
| WO | WO 2012-057689 | 5/2012 |

OTHER PUBLICATIONS

Berth et al., The state of the art in the analysis of two-dimensional gel electrophoresis images, Appl Microbiol Biotechnol (2007) 76:1223-1243.*
Hanumantharaju et al., Adaptive Color Image Enhancement based Geometric Mean Filter, ICCCS '11 Proceedings of the 2011 International Conference on Communication, Computing & Security, 2011, 403-408.*
BioRad, Quantity One User Guide, 2000, 401 pages, retrieved from http://www.calpoly.edu/~bio/ubl/equip_files/q1_manual.pdf on Sep. 11, 2015.*
Kuczius, T., et al., Analytical Biochemistry, vol. 409, 2011, pp. 260-266.
Li, Y., et al., Biochemical and Biophysical Research Communications, vol. 386, 2009, pp. 488-492.
"Nothing matches Ettan DIGE for accuracy" Amersham Biosciences, 18-1176-07 AA[online] retrieved Dec. 21, 2011, from http://juang.bst.ntu.edu.tw/Protein/proteomics/files/Ettan%20DIGE.pdf.
Leimgruber, R., et al., Proteomics, vol. 2, 2002, 135-144.
"Quantitative Imaging Solutions" GE Healthcare, 28-9419-67 AC Feb. 2010, [online] retrieved Dec. 19, 2011 from http://www.gelifesciences.com/aptrix/upp00919.nsf/Content/C2814EF605C93E9FC125762B0039150D/$file/28941967AC.pdf.
"Amersham ECL Plex Western blotting system" GE Healthcare, PA43009PL Rev AD Feb. 2011[online] retrieved Dec. 1, 2011, from http://www.gelifesciences.com/aptrix/upp00919.nsf/Content/3EBED343C9A21915C125786B00827C38/$file/28994582AD.pdf.
Supplementary European Search Report for European Application No. 12803774.4 dated Mar. 5, 2015.

* cited by examiner

*Primary Examiner* — Andrea S Grossman
(74) *Attorney, Agent, or Firm* — Eversheds Sutherland (US) LLP

(57) ABSTRACT

The present invention relates to a method for identification of specific target proteins in a protein sample following a detection procedure, such as a Western blotting procedure, wherein the membrane is probed with at least two primary antibodies directed against the same and/or different epitopes of the same target protein, and wherein specific binding to the target protein in a sample is differentiated from unspecific binding to the target protein by comparing the resulting sample patterns, such as bands or spot patterns, with each other.
In a further step signals from the true target proteins are enhanced while signals resulting from unspecific binding are diminished.

21 Claims, 3 Drawing Sheets

METHOD FOR SPECIFIC IDENTIFICATION OF TARGET BIOMOLECULES

CROSS-REFERENCE TO RELATED APPLICATIONS

This application is a filing under 35 U.S.C. 371 of international application number PCT/SE2012/050728, filed Jun. 27, 2012, published on Jan. 3, 2013 as WO 2013/002723, which claims priority to application number 1150599-7 filed in Sweden on Jun. 29, 2011.

FIELD OF THE INVENTION

The present invention relates to a method for specific identification of target biomolecules in a sample leading to improved specificity in especially multiplexed Western blotting assay formats. The method uses at least two probes directed against the same or different epitopes of the target biomolecule. In a further step signals from the true target biomolecule are enhanced while signals resulting from unspecific binding are diminished.

BACKGROUND OF THE INVENTION

Western blotting (or, protein immunoblotting) is an analytical technique used to detect specific proteins in a given sample of tissue homogenate, cell lysate or other protein containing samples. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein. For certain applications, the proteins are probed in the gel without a transfer step. However, further description of western blot methodology is based on protein samples transferred to a membrane.

During the detection process the membrane is probed for the protein of interest by the use of an antibody specific for the protein of interest. Due to possibilities of increased signal amplification and to avoid negative effects on target specific affinity related to primary antibody conjugation, this traditionally takes place in a two-step process (using a primary target specific antibody and a secondary labeled antibody specific for the primary antibody), although there are now one-step detection methods available for certain applications. The one-step method allows the process to occur faster and with a lower amount of consumables, but sensitivity and specificity may be compromised. This requires a probe antibody which both recognizes the protein of interest and contains a detectable label, probes which are often available for known protein tags. The primary probe is incubated with the membrane in a manner similar to that for the primary antibody in a two-step process, and is then ready for direct detection after a series of wash steps.

Preparing or raising antibodies against a partly purified target protein or proteins with weak immunogenic properties may result in low immuno-specificity and antibodies from suppliers are not always of sufficiently high quality. Affinity purification could be used to overcome the problem, but requires purified target protein and involves risks with sample handling including e.g. loss of antibody, activity and stability issues. Improper storage and aged antibodies can give similar reduced detection performance. When a protein target (mw size may be unknown) is lacking specific antibodies of high quality, the true immunogenic protein band corresponding to the target is very difficult to determine in a conventional Western blotting experiment.

For many target proteins there is a limited availability of highly specific antibodies, resulting in a Western blot assay with low specificity. This may lead to that it is impossible to identify correct band when molecular weight of target protein is unknown. Also there is a risk of identifying the wrong band if unspecific bands are located close to the specific band, particularly if the unspecific bands are prominent. This may be a problem even when the molecular weight of the target protein is known.

Thus, there is a need of improved methods for increasing the specificity in the identification of target proteins especially in Western blotting assay formats.

SUMMARY OF THE INVENTION

In a first aspect the present invention provides a method for identification of specific target biomolecules in a sample following a detection procedure (such as a Western blotting procedure, a biotin-streptavidin/avidin based assay, non-reducing gel electrophoresis, reducing electrophoresis, capillary electrophoresis, chip electrophoresis, isoelectric focusing, 2D electrophoresis or any detection procedure involving separation of biomolecules based on physical or chemical properties), wherein a gel or membrane is probed with at least two probes (such as antibodies, fragments thereof (Fab, F(ab')$_2$ or Fc fragment specifically binding to the target biomolecule), or other affinity binders, such as aptamers), directed against the same and/or different sites (such as epitopes when antibodies are used as probes) of the same target biomolecule, and wherein specific binding to the target biomolecule in a sample is differentiated from unspecific binding to the target biomolecule by comparing the resulting sample patterns (such as bands or spot patterns on a gel or membrane) with each other.

Preferably the sample patterns obtained from the detection procedure are compared by overlapping.

In a preferred embodiment of the method the detection procedure is a Western blotting procedure and the method comprises enhancing overlapping band features and sorting out non-overlapping features to produce image data with a pattern more specifically representing the target protein.

The method is not limited to any special target biomolecule but it is preferably a protein, peptide or aggregated biomolecule, such as a fusion protein, or a modified protein, such as a phosphorylated, glycosylated, ubiquitinated, SUMOylated, or acetylated protein.

Preferably an algorithm is used to enhance overlapping band features, such as by pixel-wise multiplication. The resulting image data is preferably scaled after the enhancement, for example using the square root function. Another example of scaling is by using an $A^{1/n}$ function where A is the resulting pixel value after enhancement and n is the number of primary antibodies. A further example of scaling is by using a function involving image data from the original images.

The image data resulting from the method of the invention may be represented in the form of one or more intensity profiles or 3D surfaces. The final result may also be presented in the form of one or more images where optionally color coding has been used to highlight overlapping and/or non-overlapping features. The color coding may represent the result of applying an algorithm to image data.

When the detection procedure is Western blotting, preferably at least two primary antibodies are used as probes.

These may be from different species or from the same species. In one embodiment the primary antibodies are differentially labelled.

In another embodiment labelled secondary antibodies are used against said primary antibodies.

The primary or secondary antibodies used in the method of the invention may be labelled with fluorescent dyes, preferably cyanine dyes. One or more of the antibodies may be detected using Enhanced chemiluminescence (ECL) to provide multiplexing.

Multiplexing may also be provided by an antibody stripping and re-probing procedure.

In a further embodiment of the method, one or more of the sample patterns represent detection using a specific or non-specific post stain.

In yet a further embodiment of the method, one or more of the sample patterns represent detection using specific or non-specific protein labeling.

In the method according to the invention, at least two sample patterns may represent different samples covalently labeled with different dyes and mixed together before electrophoresis is carried out. Alternatively at least two images may represent different pre-processing of sample aliquots covalently labeled with different dyes and mixed together before electrophoresis is carried out, wherein the pre-processing for example may involve affinity separation, for example using antibodies against the target protein.

In the method according to the invention the resulting sample pattern may be quantitatively analyzed.

Finally, the method of the invention may be implemented in a software package and/or in an instrument system, such as an instrument system for Western blotting analysis.

DETAILED DESCRIPTION OF THE INVENTION

Figure 1:
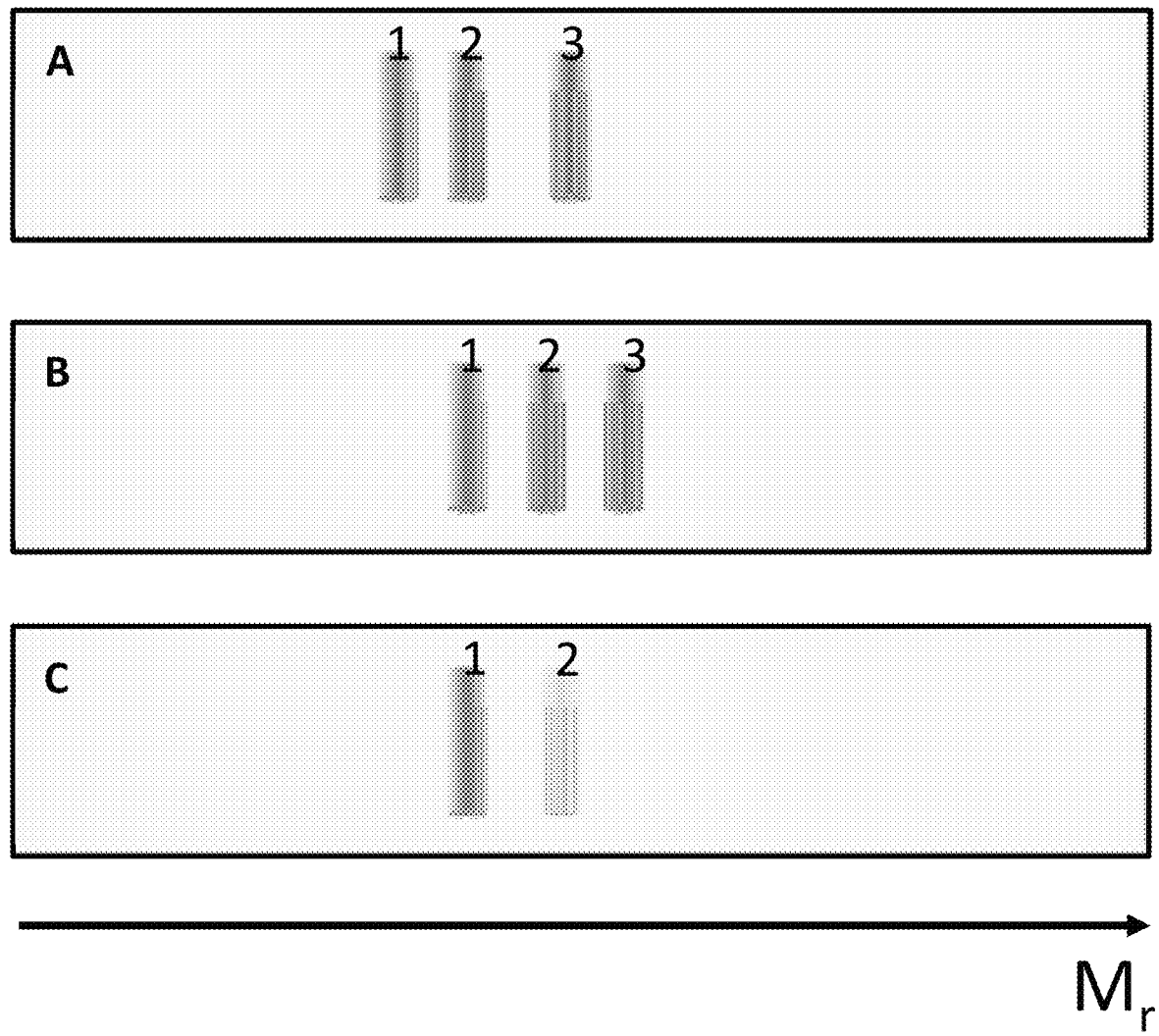
FIG. 1 shows the results of applying the method of the invention including a proposed algorithm to a multiplexed Western blotting experiment.

Western blotting is one of the most widely used assays for identification of specific target proteins in a protein sample. The present invention provides not only improved quantitative comparison but also improves the specificity of the assay.

The present invention uses several probes, preferably antibodies, directed against the same or different epitopes of the same target protein. These antibodies may be more or less specific. Since the method of the invention combines the signals from the different antibodies, specific signal can be discriminated from unspecific ones.

An example of the method may be summarized as follows:
1. Obtain at least two antibodies directed against the same, or different epitopes of the target protein, wherein the antibodies preferably are produced in different species.
2. Use the different antibodies in (1) as primary Ab's in a multiplexed Western blotting assay. The reporter dye or molecule may be conjugated to primary antibodies or to secondary antibodies directed against primary antibodies from different species.
3. The Western blotting patterns for the different antibodies recognizing the true target protein, by binding to the same or to different epitopes, will overlap perfectly while patterns resulting from binding to other proteins in an unspecific manner, including e.g. fragments and variants will only overlap by chance.
4. Evaluate the result using an algorithm that enhances the overlapping band features and points out the non-overlapping features to produce an image with a Western blotting pattern more specifically representing the target protein(s). The specific target protein levels can be analyzed quantitatively and the physical properties can be determined (Mw, pI etc). See also FIG. 1 below.

A more detailed example of an algorithm for the purpose described above for two antibodies is:

$$P_t(n) = SQRT(P_1(n) \cdot P_2(n))$$

where $P_t(n)$ is the signal intensity in an image pixel (n) representing the target protein Western pattern.

$P_1(n)$ is corresponding value from an image representing the Western pattern from the first Ab.

$P_2(n)$ is corresponding value from an image representing the Western pattern from the second Ab.

The algorithm has been designed to allow also for quantitative comparison of target protein between samples. The algorithm can easily be extended to more than two antibodies. The algorithm can be adjusted to have higher discriminating power but probably on the expense of quantitative performance.

The method of the invention is especially useful in the following situations:
1. For antibodies of lower quality it is common with unspecific detection but it is not likely that different antibodies will detect the same unspecific bands. Multiplexed co-detection using two or more different antibodies raised against the same target protein will improve analysis specificity by combining the over laid specific signals and removing non-overlapping unspecific signals. The co-detection even enables removal of any unspecific band in close vicinity to a specific band of known molecular weight, which with current methods creates uncertainty.
2. The size of the specific protein may be unknown due to unknown identity, molecular weight isoforms, or if the protein is fragmented. It is then possible to combine two or more different antibodies for confirmation of identity of target related protein bands by multiplexed co-detection.
3. Epitope (or PTM) mapping is possible by combining epitope specific antibodies (or labels or stains) with an antibody (or label or stain) detecting general overall part of the target. Epitopes can also be mapped to isoforms or fragments of the target protein using two or more different antibodies by multiplexed co-detection.
4. When the physical properties of the target protein (Mw, pI etc) are unknown, for example during purification e.g. by using chromatography based on activity or any other functional property. An antibody produced against a protein which is not entirely pure is likely to result in reduced quality and specificity of antibody. The co-detection enables removal of any unspecific bands and thereby simplifies identification of the physical properties (Mw, pI etc) of the specific protein band.

Materials and Methods

A 2-fold dilution series of PDGF induced cell lysate CCD-1064SK (Santa Cruz Biotechnology, Inc.), from 10 to 1.25 µg was mixed with 2×SLB (0.125 M Tris-HCl, pH 6.8, 4% SDS, 17.4% Glycerol, 0.2 mg/ml Bromophenol blue, 31 mg/ml DTT), heated at 96° C. for 5 minutes and applied to a Novex® 12% Tris-glycine pre-cast gel (Invitrogen). The electrophoresis (MiniVE vertical Electrophoresis system, GE Healthcare) was performed at 100 V until the bromophenol blue front reached the end of the gel. ECL Plex Fluorescent Rainbow Markers (GE Healthcare) was used to track the separation. The gel was equilibrated in transfer buffer (1×Tris-glycine, 20% Methanol) for 15 minutes before transfer onto a PVDF membrane (Hybond-LFP, GE Healthcare) using the TE 22 Mini tank transfer unit (GE Healthcare) at 25 V and 4° C. for 2.5 h. The membrane was blocked in 2% (w/v) ECL Advance blocking agent (GE Healthcare) for 1 h at room temperature. After blocking, the membrane was rinsed twice and washed for 2×5 min in PBS buffer with 0.1% Tween20 (PBST). The membrane was incubated with monoclonal mouse anti tubulin (Sigma Aldrich) and rabbit anti tubulin, whole antiserum extract (Sigma Aldrich) primary antibodies at 1:2000 and 1:1000 dilution in PBST respectively over night at 4° C. The membrane was rinsed twice and then washed for 2×5 min in PBST and incubated with ECL Plex goat anti-mouse IgG, Cy5 (GE Healthcare) and ECL Plex goat anti-rabbit IgG, Cy3 (GE Healthcare) secondary antibodies dilutes of 1:2500 in PBST for 1 h at room temperature. After four brief rinses and 4×5 min washing in PBST the membrane was rinsed four times in PBS without Tween20 and finally dried overnight (protected from light) before scanned in Cy3 and Cy5 detection channels at a resolution of 100 µm using the Typhoon 9400 (GE Healthcare). The 16 bit Gel image data from the Typhoon scanner was analyzed using the ImageJ software, (National Institutes of Health, USA), version 1.45h.

Results

FIG. 1 illustrates the effect of combining the information in two schematic Western blotting membrane images A and B to produce a combined image C. Images A and B represent Western blot patterns from two different antibodies intended to target the same protein, detected in the same membrane using color multiplexing. Image C is formed by pixel wise multiplication of images A and B after background subtraction. It is obvious that bands representing non-specific binding and therefore not present in both images A and B, i.e. bands 1 and 3 in image A and bands 2 and 3 in image B are heavily suppressed in the resulting image C. The band representing the specific binding is present in both images A and B, i.e. band 2 in image A and band 1 in image B, and is therefore not suppressed in the resulting image 3 where it is labeled as band 1.

Figure 2:
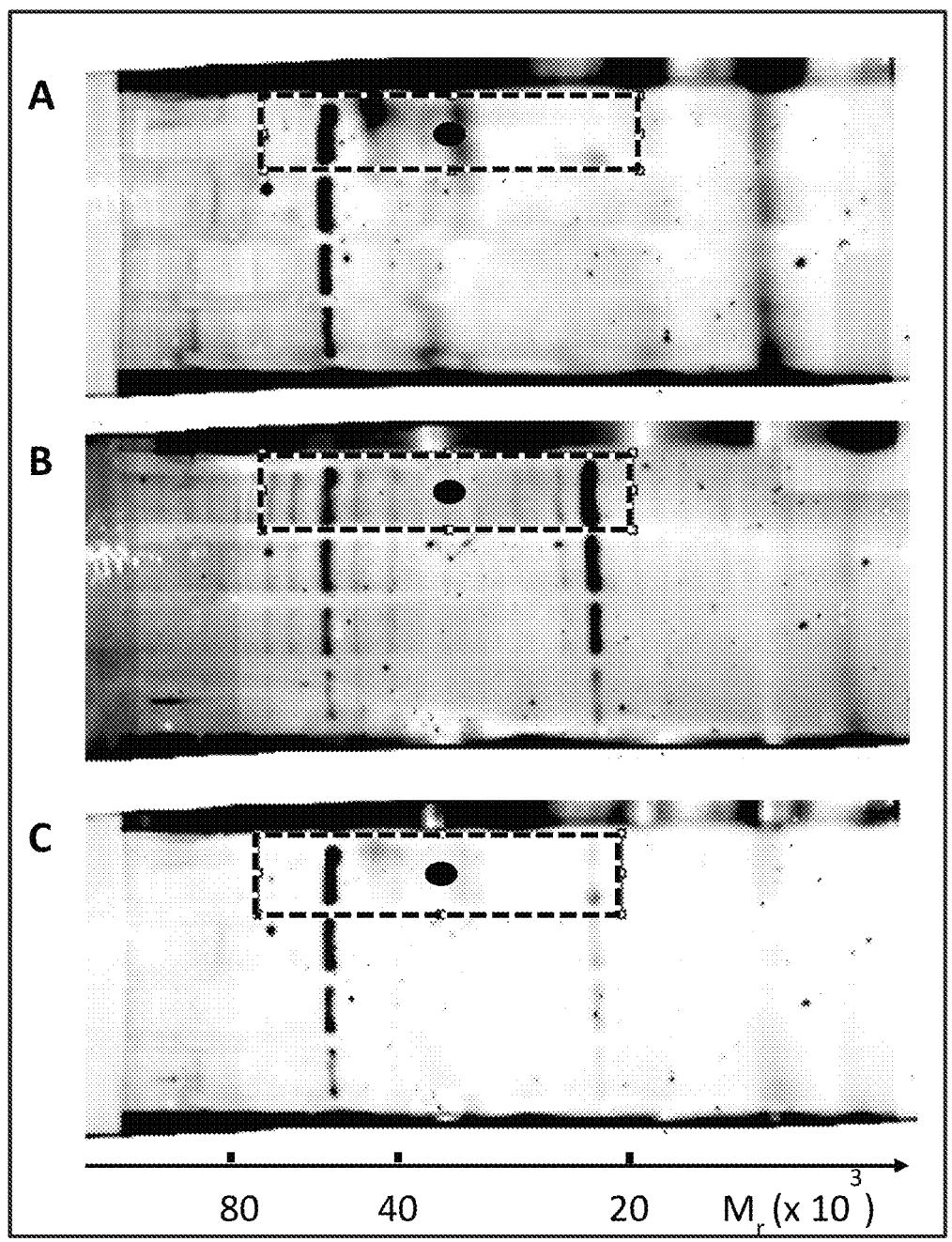
FIG. 2 shows results of a color multiplexed Western experiment described in the Detailed description of the invention.

FIG. 2 shows the result of the color multiplexed Western experiment where image A represents the Western signals from monoclonal mouse anti-tubulin (detected using a Cy5 conjugated anti-mouse IgG secondary antibody) and image B represents the Western signals from rabbit anti-tubulin whole antiserum (detected using a Cy3 conjugated anti-rabbit IgG secondary antibody). Image C is formed by pixel wise multiplication of images A and B after background subtraction. It is obvious that only band features prominent in both images A and B will become prominent also in image C. Many non-specific band features will therefore be suppressed in image C. The intensity profiles corresponding to the outlined lanes in images A-C (outlined by dashed lines) are presented in FIG. 3. Relative migration positions (Mr) based on molecular weight standards are indicated.

The images were analyzed to determine if the proposed algorithm can provide increased specificity by combining information from Cy3 and Cy5 images from the multiplexed membrane. The images were imported into ImageJ (FIGS. 2A and 2B) and the background was subtracted using the rolling ball method with a radius of 200 pixels. After background subtraction pixel intensities in each image were multiplied with each other to generate a new image (FIG. 2C). Lane profiles for the lane corresponding to 10 µg cell lysate, indicated by dashed lines, were created for each image and the corresponding lane intensity was plotted against the position as presented in FIG. 3A-C.

Figure 3:
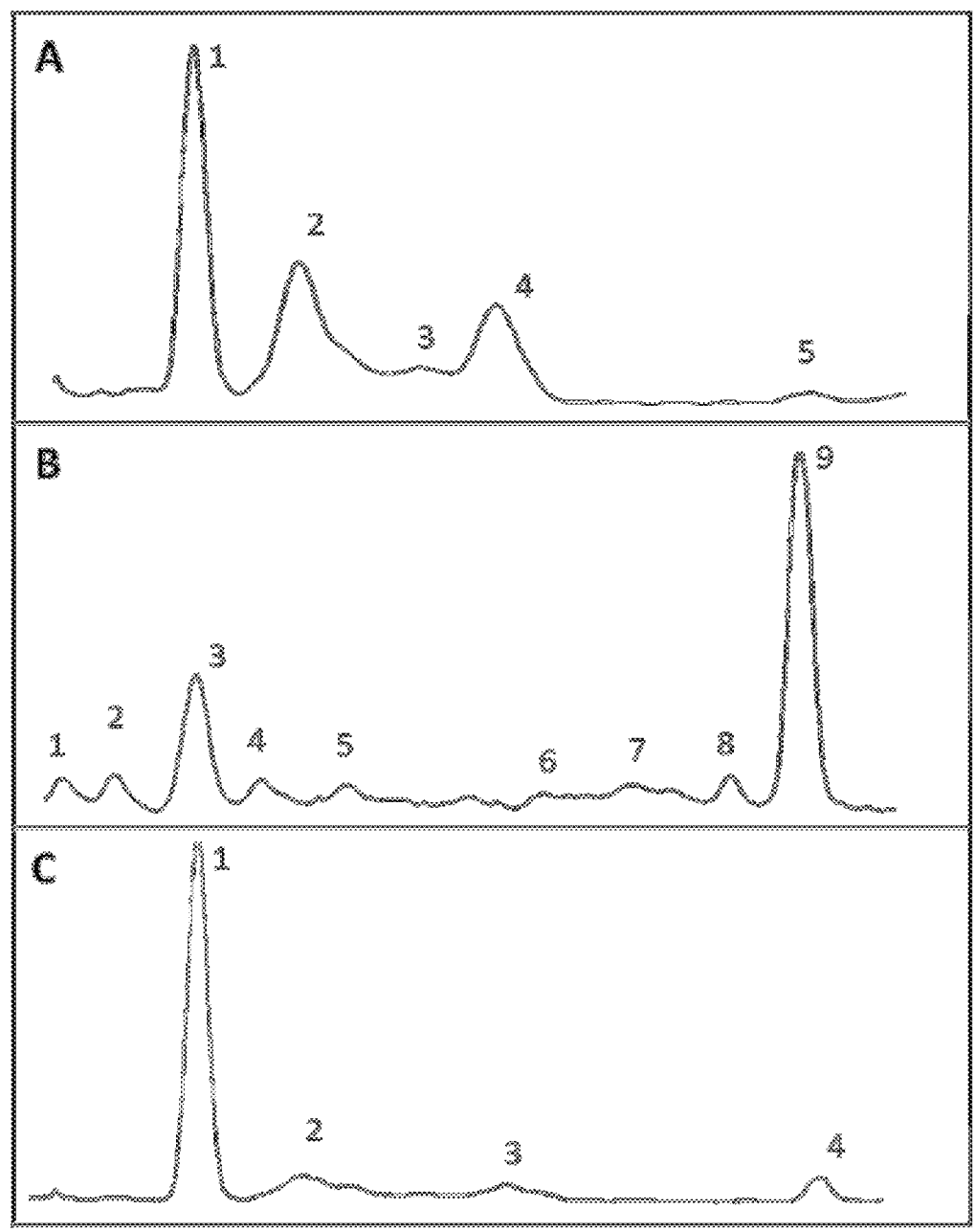
FIG. 3 shows graphs of the intensity profiles corresponding to the lanes outlined in FIG. 2.

FIG. 3 shows the intensity profiles corresponding to the lanes outlined in FIG. 2. Curve A represents the Western signal intensity profile from monoclonal mouse anti-tubulin (detected using a Cy5 conjugated anti-mouse IgG secondary antibody). Peak 1 represents the specific response from the antibody against tubulin (Mw of 55 kDa) while peaks 2-5 represent unspecifically detected proteins or artifacts.

Curve B represents the Western signal intensity profile from rabbit anti-tubulin whole antiserum (detected using a Cy3 conjugated secondary anti-rabbit IgG antibody). Peak 3 represents the specific response against tubulin while peaks 1, 2 and 4-9 represent unspecifically detected proteins of artifacts.

Curve C represents the corresponding intensity profile for image C. As can be seen there is only one prominent peak present, peak 1, which represents the specific response to tubulin. Peaks 2-4 are strongly suppressed and represent peaks 2 and 4 in curve A and peak 9 in curve B respectively. Unspecific signals generated by either the antibody binding to other proteins than the protein of interest, contamination by the ladder or dust from the scanner were reduced in the resulting lane profile.

The invention claimed is:

1. A method for identification of specific target biomolecules in a sample in a detection procedure, comprising:
    probing a gel or membrane with at least two probes that are directed against and specifically bind to a same target biomolecule to form bands or spot patterns on the gel or membrane;
    obtaining image sample patterns corresponding to the bands or spot patterns;
    overlaying the image sample patterns with each other;
    generating image data by applying an algorithm that uses pixel-wise multiplication to enhance overlapping features and diminish non-overlapping features of the bands or spot patterns in the overlayed image sample patterns;
    scaling the image data using a root function; and
    differentiating the bands or spot patterns corresponding to specific binding of the probes to the target biomolecule in the sample from non-specific binding of the probes to other biomolecules in the sample using the scaled image data.

2. The method of claim 1, wherein the target biomolecule is a protein, a peptide, an aggregated biomolecule, a fusion protein, a modified protein, a phosphorylated protein, a glycosylated protein, an ubiquitinated protein, a SUMOylated protein, or an acetylated protein.

3. The method of claim 1, wherein the scaling of the image data uses a function involving image data from original images.

4. The method of claim 1, wherein the resulting sample pattern is quantitatively analyzed.

5. The method of claim 1, further comprising:
    pre-processing the sample; and separating the sample by electrophoresis after the pre-processing step.

6. The method of claim 5, wherein the pre-processing of the sample comprises affinity separation by using antibodies against the target biomolecule.

7. The method of claim 5, wherein at least two images represent aliquots of a sample that have been covalently labeled with different dyes and mixed together during the pre-processing of the sample.

8. The method of claim 1, wherein the detection procedure is a Western blotting procedure.

9. The method of claim 8, wherein the image data is in a form of one or more intensity profiles or 3D surfaces.

10. The method of claim 8, wherein the image data is in a form of one or more 3D surfaces.

11. The method of claim 1, wherein a final result is the image data presented in a form of one or more images where color coding has been used to highlight the overlapping and/or non-overlapping features of the bands or spot patterns.

12. The method of claim 11, wherein the color coding represents a result of applying the algorithm to the image data.

13. The method of claim 1, wherein at least two primary antibodies are used as probes.

14. The method of claim 13, wherein the at least two primary antibodies are from different species.

15. The method of claim 13, wherein the at least two primary antibodies are from the same species.

16. The method of claim 13, wherein the at least two primary antibodies are differentially labelled.

17. The method of claim 13, wherein one or more of the antibodies are detected using Enhanced chemiluminescence (ECL).

18. The method of claim 13, wherein the primary antibodies are labeled with fluorescent dyes.

19. The method of claim 13, wherein differentially labelled secondary antibodies are used against the at least two primary antibodies.

20. The method of claim 19, wherein the secondary antibodies are labeled with fluorescent dyes.

21. The method of claim 20, wherein the fluorescent dyes are cyanine dyes.

* * * * *